(12) United States Patent
Emtell et al.

(10) Patent No.: US 8,701,458 B2
(45) Date of Patent: Apr. 22, 2014

(54) ON-DEMAND GAS REGULATOR FOR GAS ANALYZER CALIBRATION

(75) Inventors: Pär Emtell, Vällingby (SE); Mikael Kock, Åkersberga (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 13/377,002

(22) PCT Filed: Jun. 11, 2009

(86) PCT No.: PCT/SE2009/050712
§ 371 (c)(1),
(2), (4) Date: Feb. 27, 2012

(87) PCT Pub. No.: WO2010/144005
PCT Pub. Date: Dec. 16, 2010

(65) Prior Publication Data
US 2012/0151986 A1 Jun. 21, 2012

(51) Int. Cl.
*G01N 21/00* (2006.01)
*G01N 27/00* (2006.01)
*G01N 31/00* (2006.01)
*G01N 33/00* (2006.01)
*G01N 35/00* (2006.01)
*G01N 37/00* (2006.01)

(52) U.S. Cl.
USPC ..................... 73/1.06; 137/505.13

(58) Field of Classification Search
USPC ..................... 73/1.06; 137/505.13
See application file for complete search history.

(56) References Cited

U.S. PATENT DOCUMENTS

| | | | | |
|---|---|---|---|---|
| 6,082,398 A | * | 7/2000 | Girard et al. | 137/599.01 |
| 7,013,703 B2 | * | 3/2006 | Derek et al. | 73/1.73 |
| 7,260,976 B2 | * | 8/2007 | Colman et al. | 73/1.06 |
| 7,429,358 B1 | * | 9/2008 | Gross | 422/83 |
| 2003/0216660 A1 | | 11/2003 | Ben-Oren et al. | |
| 2004/0025940 A1 | * | 2/2004 | Chang et al. | 137/487.5 |
| 2006/0225795 A1 | * | 10/2006 | Baker | 137/614.19 |

FOREIGN PATENT DOCUMENTS

GB   2 040 715 A   9/1980
GB   2040715 A   *   9/1980   .............. B01F 15/04

\* cited by examiner

*Primary Examiner* — Lisa Caputo
*Assistant Examiner* — Jamel Williams
(74) *Attorney, Agent, or Firm* — Schiff Hardin LLP (57) ABSTRACT

A gas regulating device for use in calibration of a gas analyzer has an inlet and an outlet, a valve arrangement comprising at least one valve, and valve regulator for regulating the at least one valve. The gas regulating device is intended to be connected between a calibration gas supply and a gas analyzer that is to be calibrated and the valve regulator is configured to regulate the at least one valve such that gas is allowed to flow through a gas flow path between the inlet and outlet only when a gas pressure in the gas flow path, between the at least one valve and the outlet, falls below a predetermined threshold value. The gas regulating device is used when calibrating side-stream gas analyzers in which case it reduces calibration gas consumption, prevents discharge of calibration gas into the ambient environment and prevents leakages jeopardizing correct calibration.

11 Claims, 5 Drawing Sheets

ON-DEMAND GAS REGULATOR FOR GAS ANALYZER CALIBRATION

BACKGROUND OF THE INVENTION

1. Field of the Invention

The present invention relates to a gas regulating device for use in calibration of a gas analyzer, calibration arrangements for use in calibration of a gas analyzer, a method for calibrating a gas analyzer, and use of a gas regulating device for calibration of a gas analyzer.

2. Description of the Prior Art

Gas analyzers are well known in the art and often used in various breathing assist devices such as ventilators and anesthetic machines to analyze the composition of breathing gases supplied to a patient and/or the composition of gases exhaled by the patient.

There are mainly two types of gas analyzers used for this purpose; in-line gas analyzers and side-stream gas analyzers.

An in-line gas analyzer, sometimes also referred to as a main stream gas analyzer, is positioned in the gas flow path of the breathing assist device, normally by connecting the gas analyzer in line with the gas-conducting tubing of the breathing assist device. Thereby, an in-line gas analyzer is automatically traversed by the gas that is to be analyzed.

A side-stream analyzer on the other hand is connected to the gas flow path of the breathing assist device through a side connection, for example a side connection in form of a thin hose connecting the side-stream gas analyzer with the Y-piece of the breathing assist device. Normally, a side-stream gas analyzer is hence not automatically traversed by the gas that is to be analyzed. Therefore, a side-stream gas analyzer typically comprises a pump or other flow generating means in order to "suck" the gas that is to be analyzed from the gas flow path of the breathing device to the measurement chamber of the gas analyzer where the gas is analyzed. Typically, a side-stream gas analyzer operates at a working flow in the range of 0 to 500 ml/minute, meaning that the flow generating means of the side-stream gas analyzer is adapted to generate a flow within that range.

In order to ensure reliable operation of gas analyzers they should be regularly maintained and calibrated. Calibration is typically performed once a year or so by connecting the gas analyzer to a calibration gas supply, typically in form of a gas cylinder comprising calibration gas having a very well-defined chemical composition. The gas analyzer is then calibrated such that the gas composition as determined by the gas analyzer corresponds to the well-defined composition of the calibration gas.

Known calibration arrangements used for calibrating side-stream gas analyzers suffer from disadvantages, some of which will be described below with reference to FIGS. 1 and 2.

Figure 1:
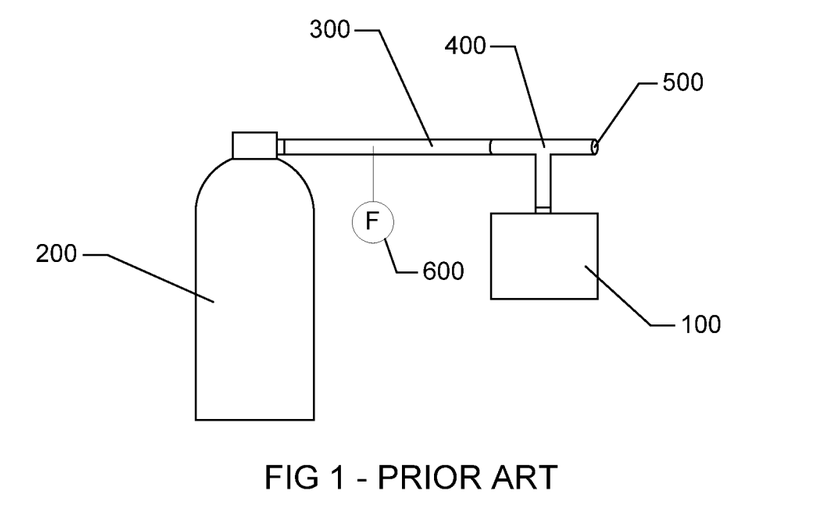
FIGS. 1 and 2 illustrate prior-art calibration arrangements for calibrating gas analyzers.

FIG. 1 illustrates a calibration arrangement according to prior art for calibrating a side-stream gas analyzer 100. The side-stream gas analyzer is simply connected to a calibration gas supply in form of a gas cylinder 200, via a hose 300 and a T-piece 400. If the gas flow provided by the calibration gas supply 200 is below the working flow of the side-stream gas analyzer 100, the gas analyzer will start sucking ambient air through the open end 500 of the T-piece, which air will mix with the calibration gas and lead to inaccurate calibration of the gas analyzer. Of course, this is also what happens if the calibration gas cylinder 200 runs out of gas. If, on the other hand, the gas flow provided by the calibration gas supply 200 is too high, excess calibration gas will be discharged to the ambient environment through the free end 500 of the T-piece, which free end hence serves as an excess calibration gas outlet. This is an undesired scenario since a large volume of expensive calibration gas is wasted, which calibration gas, depending on the composition of the calibration gas, further may be inappropriate to release into the ambient environment. Some of these problems can be mitigated, at least to some extent, by connecting a flow meter 600 between the calibration gas supply 200 and the gas analyzer 100 so as to help a user of the calibration arrangement to adjust the supply of calibration gas to a suitable level. However, there will always be either a leakage of excess calibration gas, or an intake of ambient air, through the free end 500 of the T-piece.

Figure 2:
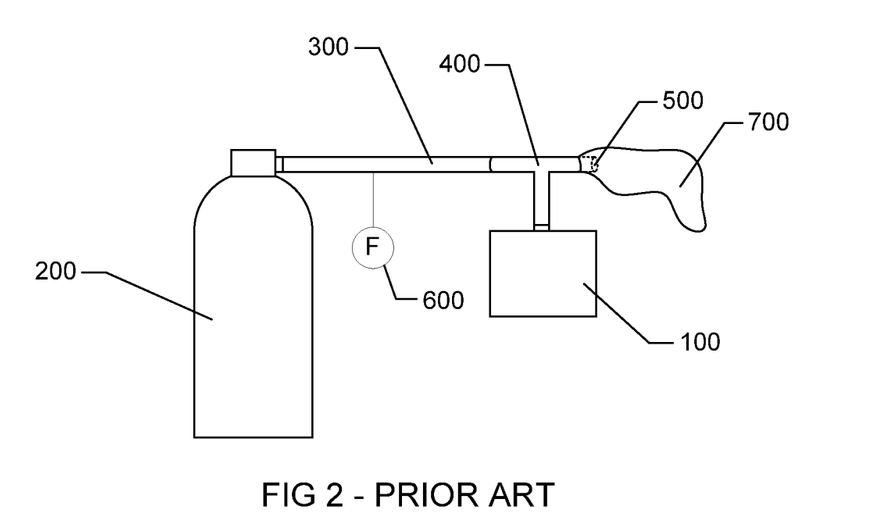

To solve the problems of undesired mixing of ambient air and calibration gas, and discharge of calibration gas into the ambient environment, a calibration arrangement as shown in FIG. 2 has been suggested. In this arrangement, a gas collection bag 700 is slipped onto the free end 500 of the 1-piece. However, this is not a satisfactory solution since the calibration gas collected in the bag 700 can normally not in practice be returned to the calibration gas cylinder 200, and should not be returned since there will inevitably be a change in gas composition when disconnecting the bag from the T-piece. That the composition of the calibration gas collected in the bag is changed when disconnecting the bag from the 1-piece may also induce errors in the calibration of gas analyzers if the collection bag 700 is reused between different calibration procedures.

Another problem with this calibration arrangement may arise if the calibration gas cylinder 200 runs completely out of gas. When the calibration gas cylinder 200 is run empty of calibration gas, the gas analyzer 100 will start sucking calibration gas out of the collection bag 700 until the bag too is empty. Since the gas analyzer will continue to suck in gas even when the bag 700 is empty, a small negative pressure will occur in the hose 300 and 1-piece 400. This negative pressure may cause the calibration gas cylinder to discharge some more gas, thus creating a small negative pressure also within the gas cylinder. When disconnecting the gas analyzer 100 from the port of the 1-piece to which it is connected during calibration, the negative pressure in the hose 300, 1-piece 400 and calibration gas cylinder 200 will cause ambient air to be sucked in through this 1-piece port and leak into the calibration gas cylinder 200. If the empty calibration gas cylinder 200 is erroneously used in a subsequent calibration procedure, a small amount of the air that leaked into the gas cylinder 200 may be discharged and ruin the calibration result.

SUMMARY OF THE INVENTION

It is an object of the invention to provide a solution solving or at least mitigating at least one of the above mentioned problems associated with calibration of side-stream gas analyzers.

This object is achieved by a gas regulating device for use in calibration of a gas analyzer. The gas regulating device has an inlet for receiving a flow of calibration gas from a calibration gas supply, an outlet for passing on said flow of calibration gas to the gas analyzer to be calibrated, a valve arrangement comprising at least a one valve disposed in a gas flow path through which said inlet and outlet can be brought in gaseous connection, and a valve regulator for regulating the at least one valve. The valve regulator is configured, when the gas regulating device is operated in a first operational mode, to regulate the at least one valve such that gas can flow between the inlet and outlet only when a gas pressure in the gas flow path, between the at least one valve and the outlet, falls below a predetermined threshold value.

When connecting a side-stream gas analyzer to a calibration gas supply via the gas regulating device according to the invention, the flow of calibration gas delivered by the calibration gas supply will always correspond to the working flow of the currently calibrated side-stream gas analyzer since the gas regulating device ensures that gas is only delivered to the gas analyzer "upon demand".

The gas regulating device hence serves as a demand regulator. If the flow generator of the side-stream gas analyzer does not generate a negative pressure falling under the predetermined threshold value downstream of the valve arrangement, no calibration gas is requested for and will therefore not be delivered to the gas analyzer.

Thus, by connecting the side-stream gas analyzer to the calibration gas supply via the gas regulating device according to the invention, the consumption of expensive calibration gas will be minimized. Furthermore, the gas regulating device according to the invention eliminates the need for any excess calibration gas outlet through which excess calibration gas can be discharged, thus eliminating the risk for exposing people in the immediate surroundings of the calibration arrangement to the sometimes injurious calibration gas. Another advantage of the gas regulating device according to the invention is that it eliminates the need for using 1-pieces and calibration gas collection bags during calibration procedures, thus facilitating calibration of gas analyzers. Yet another advantage is that the gas regulating device prevents suction of air into an empty gas cylinder upon disconnection of the gas analyzer, which otherwise may occur due to the small negative pressure sometimes arising inside a gas cylinder which is run completely out of gas. This is due to the fact that no negative pressure will occur downstream of the valve arrangement once the gas analyzer is removed and, therefore, the valve will be regulated to prevent any gas to flow through the gas regulating device and into the gas cylinder.

Preferably, the gas regulating device further includes a flush actuator that when actuated by a user, is configured to set the gas regulating device in a second operational mode in which the valve regulator regulates the at least one valve such that gas can flow between the inlet and outlet of the gas regulating device no matter the pressure between the valve arrangement and the outlet.

By activating the flush actuator the "on-demand functionality" provided by the gas regulating device can hence be switched off. When the flush actuator is activated, the calibration gas from the calibration gas supply will pass straight through the gas regulating device and on to the gas analyzer, even though no negative pressure exists downstream of the valve arrangement. This functionality is advantageous in that a calibration arrangement comprising the gas regulating device according to the invention can be used for both side-stream gas analyzers generating such a negative pressure by means of their integrated flow generation means, and in-line gas analyzers which normally does not include any flow generation means and, therefore, are unable to generate such a negative pressure.

The gas regulating device may hence be configured to be operated in either a first operational mode, or side-stream operational mode, in which it acts as a demand regulator, or a second operational mode, or in-line operational mode, in which the on-demand functionality is switched off.

Preferably, the valve regulating means of the gas regulating device is further configured to regulate the at least one valve of the valve arrangement such that gas can flow between the inlet and outlet only when a gas pressure in the gas flow path, between the inlet and the at least one valve, exceeds a predetermined threshold value.

This feature is advantageous in that it prevents a calibration gas supply, such as a calibration gas cylinder, connected to the gas regulating device from running completely out of gas. Since no gas can flow through the gas regulation device unless there is a certain positive pressure upstream of the valve arrangement, a certain amount of calibration gas will always remain in the calibration gas supply, thus preventing a negative pressure to occur within the calibration gas supply. Thereby, the risk that ambient air is sucked into an empty calibration gas supply due to such a negative pressure is eliminated, hence eliminating the risk that a calibration gas supply containing a non-well-defined gas mixture is used in subsequent calibration procedures.

According to one aspect of the invention, the gas regulating device further includes an on-off switching unit that when actuated by a user, is configured to set the gas regulating device in a non-operational mode in which the valve regulator regulates the at least one valve of said valve arrangement such that no gas can ever flow between said inlet and outlet.

This feature, which hence serves to set the gas regulating device in either of an 'ON' or 'OFF' mode, is particularly advantageous if the calibration gas supply does not comprise any on/off switch for the calibration gas flow. Then the gas regulating device can be put in a non-operational mode, or 'OFF' mode, before connecting it to the calibration gas supply and the gas analyzer. Thereby, assembling of the calibration arrangement is facilitated and the risk that calibration gas is undesirably discharged into the ambient environment is reduced.

Preferably, the gas regulating device according to the invention has a housing making it a self-contained unit which can be provided as an off-the-shelf product for interconnection between a calibration gas supply and a gas analyzer that is to be calibrated. In this case, the gas regulating device has an inlet connection configured to detachably connect the inlet of the gas regulating device to the calibration gas supply, and an outlet connection configured to detachably connect the outlet of the gas regulating device to the gas analyzer.

Even more preferably, the inlet connection of the gas regulating device is configured to be detachably connected directly to matching outlet connection of the calibration gas supply. Thus, according to an aspect of the invention, there is provided a calibration arrangement for use in calibration of a gas analyzer, which calibration arrangement has a calibration gas supply and a gas regulating device as described above. The calibration gas supply has an outlet connection configured to be detachably connected directly to the inlet connection of the gas regulating device.

According to an aspect of the invention the gas regulating device is realized in the form of an electronic device having a single valve controlled by a control unit based on pressure measurements obtained from one or several sensors disposed in the gas flow path. In this case, the control unit may be connected to a user input actuator of the gas regulating device, such as an on-off button and/or a flush button, and configured to set the gas regulating device in either of the first and second operational mode, or the non-operational mode, based on user input.

According to another aspect of the invention the gas regulating device is realized in form of an entirely mechanical device having one or several mechanical valves for providing the above described functionality. In this case, the gas regulating device may likewise include a user input actuator that when activated by a user, mechanically acts on the valve(s) to set the gas regulating device in any of the above modes.

The object of the invention is also achieved by a calibration arrangement for use in calibration of a gas analyzer, having a calibration gas supply having an outlet, a gas analyzer having an inlet, and a gas regulating device as described above. The inlet of the gas regulating device is connected to the outlet of the calibration gas supply and the outlet of the gas regulating device is connected to the inlet of the gas analyzer such that calibration gas can flow through a gas flow path from the outlet of the calibration gas supply to the inlet of the gas analyze, through the gas regulating device.

The object of the invention is also achieved by a method for calibrating a gas analyzer. The method includes the step of supplying a calibration gas from a calibration gas supply to the gas analyzer via a gas flow path in which a valve arrangement comprising at least one valve is disposed. The method further includes the step of regulating the at least one valve to allow gas to flow through said gas flow path only when a gas pressure in the gas flow path, downstream of the at least one valve, falls below a predetermined threshold value.

BRIEF DESCRIPTION OF THE DRAWINGS

A more complete appreciation of the invention disclosed herein will be obtained as the same becomes better understood by reference to the following detailed description when considered in conjunction with the accompanying figures briefly described below, in which drawings the same reference numerals are used to represent the same functional elements.

DESCRIPTION OF THE PREFERRED EMBODIMENTS

Figure 3:
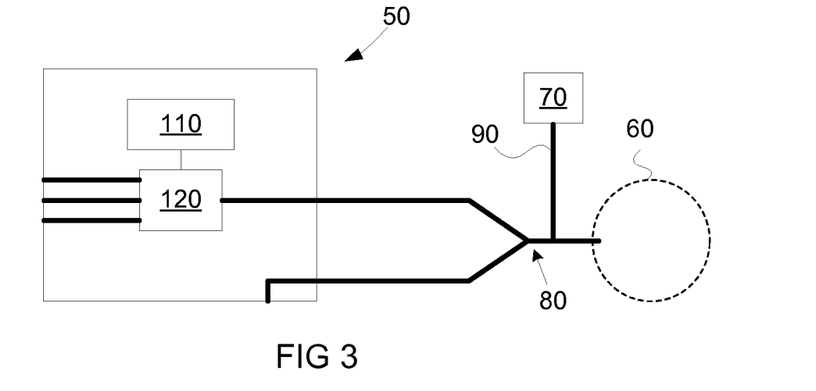
FIG. 3 illustrates a ventilator and the way a side-stream analyzer may be connected thereto.

FIG. 3 illustrates an exemplary field of application for a gas analyzer that can be calibrated using a gas regulating device according to the invention.

In FIG. 3, a ventilator 50 for mechanically ventilating a patient 60 to which the ventilator is connected is shown. A side-stream gas analyzer 70 is arranged in gaseous connection with a Y-piece 80 of the ventilator through a side connection 90. The side-stream gas analyzer includes a flow generator (not shown), such as a pump, for generating a flow of gas to be analyzed from the Y-piece, through the side connection, to the gas analyzer. The gas analyzer 70 may have a display unit for displaying the result of the gas analysis to an operator, or it may be electrically connected to an intensive care monitoring system or the like which in turn may be adapted to display information received from the gas analyzer 70 to an operator. The side-stream gas analyzer 70 may be configured to analyze the composition of the breathing gases supplied to the patient and/or the composition of the gases exhaled by the patient. Although not common, the side-stream gas analyzer 70 may also be electrically connected to a control unit 110 of the ventilator which may be configured to control a gas mixing and flow generator 120 of the ventilator based on the result of the gas analysis such that a desired breathing gas composition always is delivered to the patient 60.

Figure 4:
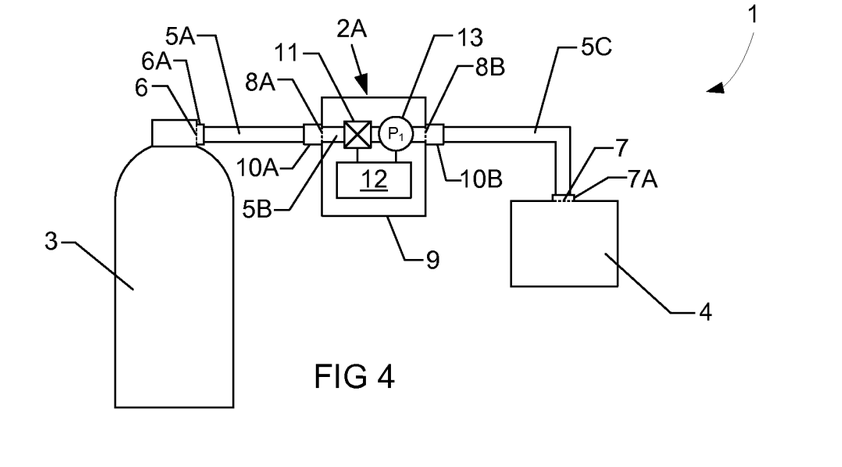
FIG. 4 illustrates a calibration arrangement and a gas regulating device according to an exemplary embodiment of the invention.

FIG. 4 illustrates a calibration arrangement 1 comprising a gas regulating device 2A according to an exemplary embodiment of the invention. The calibration arrangement 1 is further seen to have a calibration gas supply 3 in form of a calibration gas cylinder, a side-stream gas analyzer 4 that is to be calibrated, and a tube or hose arrangement 5A, 5C which, together with an interior gas flow path 5B of the gas regulating device 2A, form a gas flow path connecting an outlet 6 of the calibration gas supply 3 to an inlet 7 of the gas analyzer 4, via the gas regulating device 2A.

The gas regulating device 2A has an inlet 8A for receiving a flow of calibration gas from the calibration gas supply 3, and an outlet 8B for forwarding the calibration gas received from the calibration gas supply 3 to the side-stream gas analyzer 4. The inlet 8A and outlet 8B form openings in a housing 9 of the gas regulating device 2A, which housing makes the gas regulating device 2A a self-contained unit which can be easily connectable between existing gas calibration devices and gas analyzers. The gas regulating device 2A is equipped with an inlet connection 10A and an outlet connection 10B configured to detachably connect the inlet 8A and outlet 8B of the gas regulating device 2A to the calibration gas supply 3 and the gas analyzer 4, respectively, via the intermediate tubes or hoses 5A, 5C. The inlet connection means 10A and the outlet connection means 10B may be adapted for connection with standardized tube or hose connectors, and/or separate connector adapters (not shown) may be provided for connecting the connection means 10A, 10B of the gas regulating device 2A to different types of tubes or hoses 5A, 5C. The calibration gas supply 3 and the gas analyzer 4 are equipped with a similar outlet connection 6A and inlet connection 7A, respectively.

The inlet 8A and outlet 8B are arranged in gaseous connection with each other through a gas flow path 5B within the gas regulating device 2A. A valve arrangement, here in form of a single valve 11, is disposed in the gas flow path 5B. The valve 11 is connected to a valve regulating means, here in form of an electric control unit 12, for regulating the valve 11 so as to adjust the flow of calibration gas flowing from the inlet 8A towards the outlet 8B. The control unit 12 is further connected to a pressure sensor 13 disposed in the gas flow path 5B, downstream of the valve 11 (i.e. after the valve 11 from the gas flow's point of view), for measuring a gas pressure $P_1$. The control unit 12 is configured to receive pressure measurements from the pressure sensor 13 and to open the valve 11 only when a negative pressure (i.e. a pressure below ambient pressure) is measured. Thus, when the gas regulating device 2A is operated in a first operation mode, or normal operation mode, the control unit 12 regulates the valve 11 such that gas can flow between the inlet 8A and outlet 8B only when a negative pressure arises in the gas flow path 5B, between the valve 11 and the outlet 8B. A negative pressure arising at this location indicates that the flow generating means of the side-stream gas analyzer 4 is active and strives to suck in gas to be analyzed. Thus, the gas regulating device 2A is configured to ensure that the valve 11 remains closed unless the side-stream gas analyzer 4 "asks" for gas and hence functions as an on-demand regulator. Typically, the control unit 12 is adapted to open the valve when the pressure P1 measured by the pressure sensor 13 falls below a certain threshold value, for example a small negative pressure relative to ambient pressure, such as 10-20 mbar below ambient pressure. This threshold value will hereinafter be referred to as the negative pressure threshold value. The criterion that the valve 11 should open only if the gas pressure P1 in the gas flow path 5B between the valve 11 and the outlet 8B falls below the negative pressure threshold value will hereinafter be referred to as the on-demand criterion.

Figure 5:
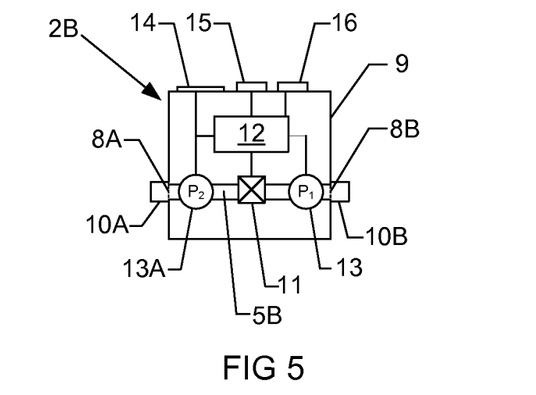
FIG. 5 illustrates another exemplary embodiment of a gas regulating device according to the invention.

FIG. 5 illustrates another embodiment of the regulator device according to the invention. In this embodiment, the gas regulating device 2B comprises a first 13 and a second 13A pressure sensor. The first pressure sensor 13 is the pressure sensor of the embodiment described above with reference to FIG. 4, and the control unit 12 is configured to regulate the valve 11 based on the pressure measurements obtained by this pressure sensor 13 in accordance with the principle described above. The second pressure sensor 13A is disposed in the gas flow path 5B, upstream of the valve 11 (i.e. before the valve 11 from the gas flow's point of view), for measuring a gas pressure $P_2$. The control unit 12 is configured to receive pressure measurements also from this second pressure sensor 13A, and to open the valve 11 only when a positive pressure (relative to ambient pressure) exceeding a certain threshold value is measured, indicating that the calibration gas supply 3 (see FIG. 3) still contains at least a minimum amount of calibration gas. Thus, according to this embodiment, the control unit 12 regulates the valve 11 such that gas can flow between the inlet 8A and outlet 8B only when a negative pressure below the negative pressure threshold value arises in the gas flow path 5B, downstream of the valve 11, and a positive pressure above a certain threshold value, hereinafter referred to as the positive pressure threshold value, arises in the gas flow path 5B, upstream of the valve 11. A suitable positive pressure threshold value may be approximately 50 mbar, which is sufficient to ensure that the valve 11 will be closed before the calibration gas supply 3 runs completely out of calibration gas. The criterion that the valve 11 should open only if the gas pressure $P_2$ in the gas flow path 5B between the inlet 8A and the valve 11 exceeds the positive pressure threshold value will hereinafter be referred to as the pressure-guard criterion.

The gas regulating device 2B further includes a manometer 14, here in form of a digital manometer. The digital manometer 14 is connected to the second pressure sensor 13A and configured to indicate the measured pressure $P_2$ on a display of the manometer 14, which pressure is indicative of the amount of calibration gas left in the calibration gas supply 3. Alternatively, the control unit 12 can be connected to a digital display (not shown) of the gas regulating device 2B and configured to display the pressure $P_2$ measured by the pressure sensor 13A on the digital display. The feature of indicating the pressure $P_2$ measured by the second pressure sensor 13A to the user of the gas regulating device 2B is particularly advantageous when the calibration gas supply itself lacks means for indicating the amount of calibration gas left.

Furthermore, the gas regulating device 2B has a flush actuator 15, for example in form of a press button or an on/off switch. The flush actuator 15, when actuated by a user, serves to set the gas regulating device 2B in a second operational mode in which the control unit 12 keeps the valve 11 open such that gas can flow between the inlet 8A and outlet 8B no matter the gas pressure $P_1$ measured by the pressure sensor 13. Activation of the flush actuator 15 hence sets the gas regulating device 2B in a flush mode in which the on-demand criterion is overruled such that the valve 11 is kept open no matter whether the pressure $P_1$ in the gas flow path 5B between the valve 11 and the outlet 8B is below the negative pressure threshold value or not. This feature is advantageous when the gas regulating device 2B is used for calibrating in-line gas analyzers which differ from side-stream gas analyzers in that they do not generate any flow by them selves. Since in-line gas analyzers do not cause any negative pressure downstream of the valve 11, the valve 11 would not open if the gas regulating device would be operated in normal operational mode. Preferably, the control unit 12 is configured such that activation of the flush actuator means 15 makes it disregard the on-demand criterion but not the pressure-guard criterion, meaning that the gas pressure $P_2$ measured by the pressure sensor 13A still must exceed the positive pressure threshold value in order for the control unit 12 to open the valve 11, even when the flush actuator 15 has been activated.

The gas regulating device 2B also has an on-off switching actuator 16, for example in form of a press button or an on/off switch. The on-off switching actuator 16 serves to set the gas regulating device 2B in either of an 'ON' or 'OFF' mode. In the 'ON' mode, the gas regulating device 2B works in normal operational mode or whatever mode the gas regulating device 2B is put in by activation of other user input actuator. When put in the 'OFF' mode, or non-operational mode, the gas regulating device 2B is configured to close the valve 11 and maintain it in a closed state. This functionality may e.g. be implemented by designing the gas regulating device 2B such that the current to an electric valve actuator (not shown) which must be powered to keep the valve 11 open is cut by shifting the on-off switching means 16 from its 'ON' state to its 'OFF' state. It may also be implemented by configuring the control unit 12 to actively close the valve 11 when the on-off switching means 16 is shifted to its 'OFF' state.

Figure 6:
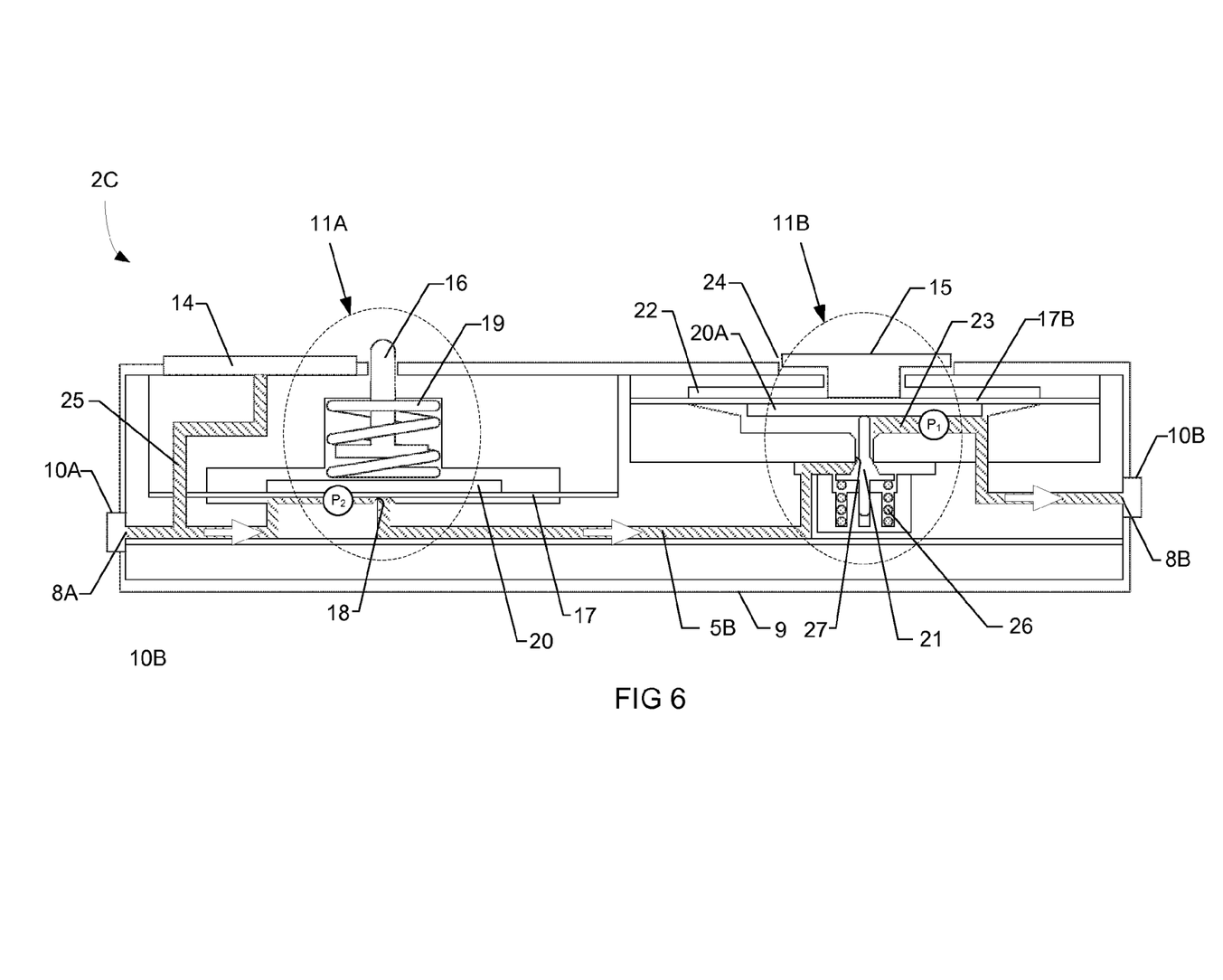
FIG. 6 illustrates yet another exemplary embodiment of a gas regulating device according to the invention.

FIG. 6 illustrates another embodiment of a gas regulating device 2C according to the invention. Whereas FIGS. 4 and 5 show embodiments according to which the gas regulating device 2A, 2B is realized as an electric device, FIG. 6 illustrates a gas regulating device 2C realized in form of a mechanical device.

The flow of calibration gas from the calibration gas supply (see FIG. 3) enters the gas regulating device 2C through the inlet 8A and is guided towards the outlet 8B via the interior gas flow path 5B of the gas regulating device. The gas flow path 5B is indicated by hatched lines and the direction of calibration gas flow is indicated by white arrows.

The gas regulating device 2C has a valve arrangement including a first valve 11A and a second valve 11B. In this embodiment, the first valve 11A is a combined pressure-guard valve and shut-off valve, whereas the second valve 11B is a combined on-demand valve and flush valve.

The first valve 11A has a spring-loaded membrane or diaphragm 17 which, when no calibration gas flows through the gas flow path 5B, closes the first valve 11A by being pressed tight against a valve seat 18 by a compressed helical spring 19. By forcing the membrane 17 into sealing-tight engagement with the valve seat 18, the helical spring 19 ensures that the first valve 11A remains closed as long as no pressure build-up occurs in the gas flow path 5B, upstream of the first valve 11A. To distribute the force applied by the spring 19 over a larger area of the membrane 17, a valve plate 20, e.g. in form of a washer or a spring washer, is arranged between the membrane-facing end of the spring 19 and the membrane 17.

When a flow of calibration gas enters the inlet 8A, the calibration gas will exert a force on the membrane 17, which force, when exceeding the spring force applied to the membrane 17 by the helical spring 19, will force the membrane 17 away from the valve seat 18 such that the calibration gas can pass through the first valve 11A. The first valve 11A hence serves as a pressure-guard valve which will remain closed unless the gas pressure $P_2$ in the gas flow path upstream of the valve exceeds a certain positive pressure threshold value, which threshold value can be chosen by choosing a suitable spring 19. The spring 19 and membrane 17 thus act as valve regulator allowing gas to flow between the inlet 8A and the outlet 8B only when the gas pressure $P_2$ in the gas flow path 5B between the inlet 8A and the first valve 11B exceeds this positive pressure threshold value.

The first valve 11A further has a mechanical on-off switching actuator 16. The on-off actuator 16 is shaped as a nail, the tip portion of which protrudes from the housing 9 to form a press button, and the head portion of which faces the valve plate 20. The on-off actuator is freely movable in the vertical direction, inside the helical spring 18. In the 'ON' state, the head of the nail-shaped on-off actuator 16 rests at a distance from the valve plate 20, allowing the calibration gas to press the membrane 17 upwards and flow through the first valve 11A. The on-off actuator is set in 'OFF' state by pressing the tip portion of the on-off actuator 16. By doing so the on-off actuator 16 is moved downwards towards the valve plate 20 and maintained in a position where the head portion of the on-off actuator 16 blocks any upward movement of the membrane 17. In the 'OFF' state, the first valve 11A is hence closed and the gas regulating device 2A is put in an 'OFF' mode in which no gas can ever flow between the inlet 8A and the outlet 8B.

It should be appreciated that this is merely an exemplary embodiment of the first valve 11A and that there are many ways known in the art to design a mechanical valve achieving the same effects. For example, according to another embodiment (not shown), the first valve 11A has a screw that is fitted in the valve such that it acts on the helical spring 19. By tightening or loosening the screw from outside the housing 9, e.g. by rotating a rotary control knob, the spring 19 can be more or less compressed, thereby allowing the positive pressure threshold value to be adjusted. By tightening the screw to an extent where the spring 19 becomes fully compressed, the membrane 17 is prevented from lifting from the valve seat 18 such that the first valve 11A will remain closed no matter the gas pressure $P_2$. Thus, according to this exemplary embodiment in which the first valve 11A is realized as a "screw-and-spring valve", the spring 19 and membrane 17 act as a valve regulator whereas the rotary control knob controlling the position of the screw acts as an on-off switching regulator which, when rotated to a position in which the screw compresses the spring 19 to a certain extent, puts the gas regulating device 2C in an 'OFF' mode in which no gas can ever flow between said inlet 8A and outlet 8B.

The second valve 11B has a spring-loaded valve body 21 that is movable between a closed position in which it blocks the gas flow path 5B such that calibration gas is prevented from flowing from the inlet 8A to the outlet 8B, and an open position in which it does not block the gas flow path 5B such that calibration gas is allowed to flow from the inlet 8A to the outlet 8B. The valve body 21 is maintained in its closed position by a compressed helical spring 26 which presses the valve body 21 against a valve seat 27. The valve body 21 is moved into its open position by the movement of a membrane or diaphragm 17B, which movement in turn is controlled by a difference between the gas pressure in a gas pocket 22 located on one side of the membrane 17B and the gas pressure $P_1$ in a portion 23 of the gas flow path 5B located on the other side of the membrane 17B, downstream of the valve body 21. In this embodiment, the gas pocket 22 is in gaseous connection with ambient air via openings 24 in the housing 9 and is thus filled with air at ambient air pressure. If the gas pressure $P_1$ in the gas flow path 5B downstream of the valve member 21 becomes negative in relation to the gas pressure in the gas pocket 22, the pressure difference on the respective sides of the membrane 17B will make the membrane 17B bend downwards and apply a pushing force to the valve body 21, via a valve plate 20A in form of a washer or spring washer attached to the underside of the membrane 17B. This force will make the valve body compress the helical spring 26 and move the valve body 21 into its open position. Thus, the helical spring 26, the membrane 17B and the valve body 21 serve as a valve regulator that regulates the second valve 17B such that gas can flow between the inlet 8A and outlet 8B only when a pressure below a predetermined threshold value occurs in the gas flow path 5B, between the second valve 11B and the outlet 8B. This threshold value thus corresponds to the previously described negative pressure threshold value and the skilled person will appreciate that the negative threshold value can be adjusted to any suitable value, e.g. by modifying the properties of the valve regulating means. Of course, the exemplary second valve 11B can be replaced by any other type of mechanical valve adapted to open only when a certain negative gas pressure occurs on one side of the valve to achieve the same effect.

The second valve 11B further has a flush actuator 15, here in form of a press button, which provides the previously described flush functionality allowing the gas regulating device 2C to be used also when calibrating in-line gas analyzers. When pressing the flush actuator 15 it will force the membrane 17B to bend downwards and force the valve body 21 into its open position as described above. Preferably, there is also provided a locking means (not shown) configured to maintain the flush actuator 15 in the active position in which the second valve 11B is kept open no matter the pressure P.

The gas regulating device 2C further includes a mechanical manometer 14 which is in gaseous connection with the gas flow path 5B via a gas channel 25 which is branched out from the gas flow path 5B at a point located between the inlet 8A and the first valve 11A. The manometer 14 will hence, when the inlet 8A of the gas regulating device 2C is connected to a calibration gas cylinder, indicate the pressure in the part of the gas flow path 5B located upstream of the first valve 11A and thus indicate the amount of calibration gas left in the calibration gas cylinder.

Figure 7A:
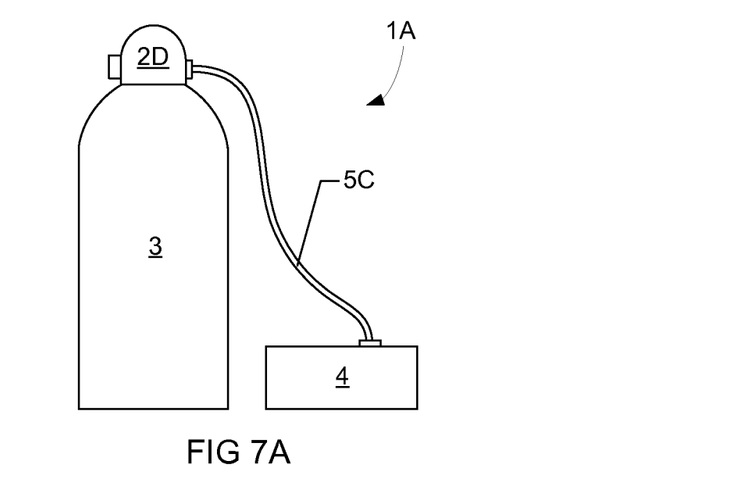
FIG. 7A illustrates a calibration arrangement and a gas regulator according to yet another exemplary embodiment of the invention.

FIG. 7A illustrates a calibration arrangement 1A according to yet another exemplary embodiment of the invention. The calibration arrangement 1A includes a gas calibration supply 3 in form of a calibration gas cylinder, a gas regulating device 2D, and a side-stream gas analyzer 4 to which the gas regulating device 2D is connected via an intermediate hose 5C.

Figure 7B:
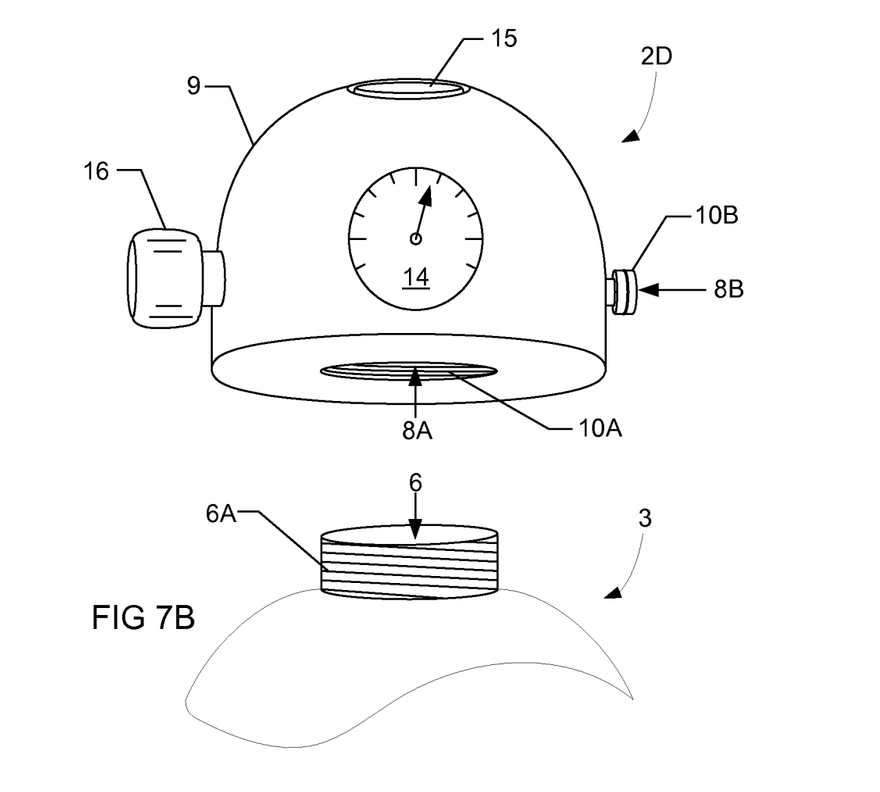
FIG. 7B shows a detailed view of the gas regulating device shown in FIG. 7A and an exemplary embodiment of an interface between a gas regulating device and a calibration gas supply according to the invention.

FIG. 7B illustrates an exterior close-up view of the gas regulating device 2D and the connection interface between the gas regulating device 2D and the gas calibration supply 3 illustrated in FIG. 7A.

In this embodiment, the gas regulating device 2D is configured to be detachably connected directly to the gas calibration cylinder 3, without any interconnecting hoses or tubes. The calibration gas cylinder 3 has an outlet connection 6A configured to be detachably connected directly to matching inlet connection 10A of the gas regulating device 3D. In this embodiment, the calibration gas cylinder 3 is provide with the outlet connection 6A in form of a protruding portion having an outer thread whereas the inlet 8A of the gas regulating device 2D is provided with an inner thread forming the inlet connection 10A of the gas regulating device 20. Thus, the outlet 6 of the gas calibration supply 3 is connected to the inlet of the gas regulating device 2D by means of a threaded engagement. It should be appreciated that many other types of gas connectors can be used to detachably connect the inlet 8A to the outlet 6.

The gas regulating device 2D may be realized as an electric device as described with reference to e.g. FIG. 4, a mechanical device as described with reference to FIG. 5, or a combination thereof. When hereinafter referring to internal components of the gas regulating device 2D or external units to which the gas regulating device 2D is connectable, reference will, when adequate, simultaneously be made to previous drawings.

The gas regulating device 2D has an outlet connection 10B for connecting the outlet 8B to an inlet 7 of a side-stream gas analyzer 4 via an intermediate hose 5C, and a manometer 14 for indicating the gas pressure $P_2$ in the gas flow path 5B upstream of a valve arrangement 11, 11A, 11B of the gas regulating device 2D. As previously mentioned, when the inlet 8A is connected to the outlet 6 of the calibration gas cylinder 3, this pressure $P_2$ corresponds to the pressure in the calibration gas cylinder 3 and hence serves as an indicator of the amount of calibration gas left. Just like the valve arrangement 11A, 11B of the gas regulating device 2C illustrated in FIG. 6, this gas regulating device 2D has a valve arrangement (not shown) including a first and second valve. These valves are disposed in a gas flow path 5B between the inlet 8A and the outlet 8B and the first valve is located upstream of the second valve (i.e. between the inlet 8A and the second valve). The first valve is a screw-and-spring valve as previously described and the second valve corresponds to the second valve 11B in FIG. 6. The gas regulating device 2D has an on-off switching actuator 16 in form of a rotary control knob mounted external to the gas regulating device housing 9. By rotating the rotary control knob the position of the screw acting on the helical spring of the first valve is adjusted, thereby allowing a user to switch on and off the gas flow through the gas regulating device 2D and set a positive pressure threshold value which must be exceeded by the pressure $P_2$ in the gas flow path 5B upstream of the first valve in order for calibration gas to pass through the gas regulating device 2D. The gas regulating device is further seen to comprise a flush actuator 15 which corresponds to flush actuator 15 in FIG. 6 and hence serves to force the second valve into an open position no matter the pressure $P_1$ in the gas flow path 5B downstream of the second valve.

Figure 8:
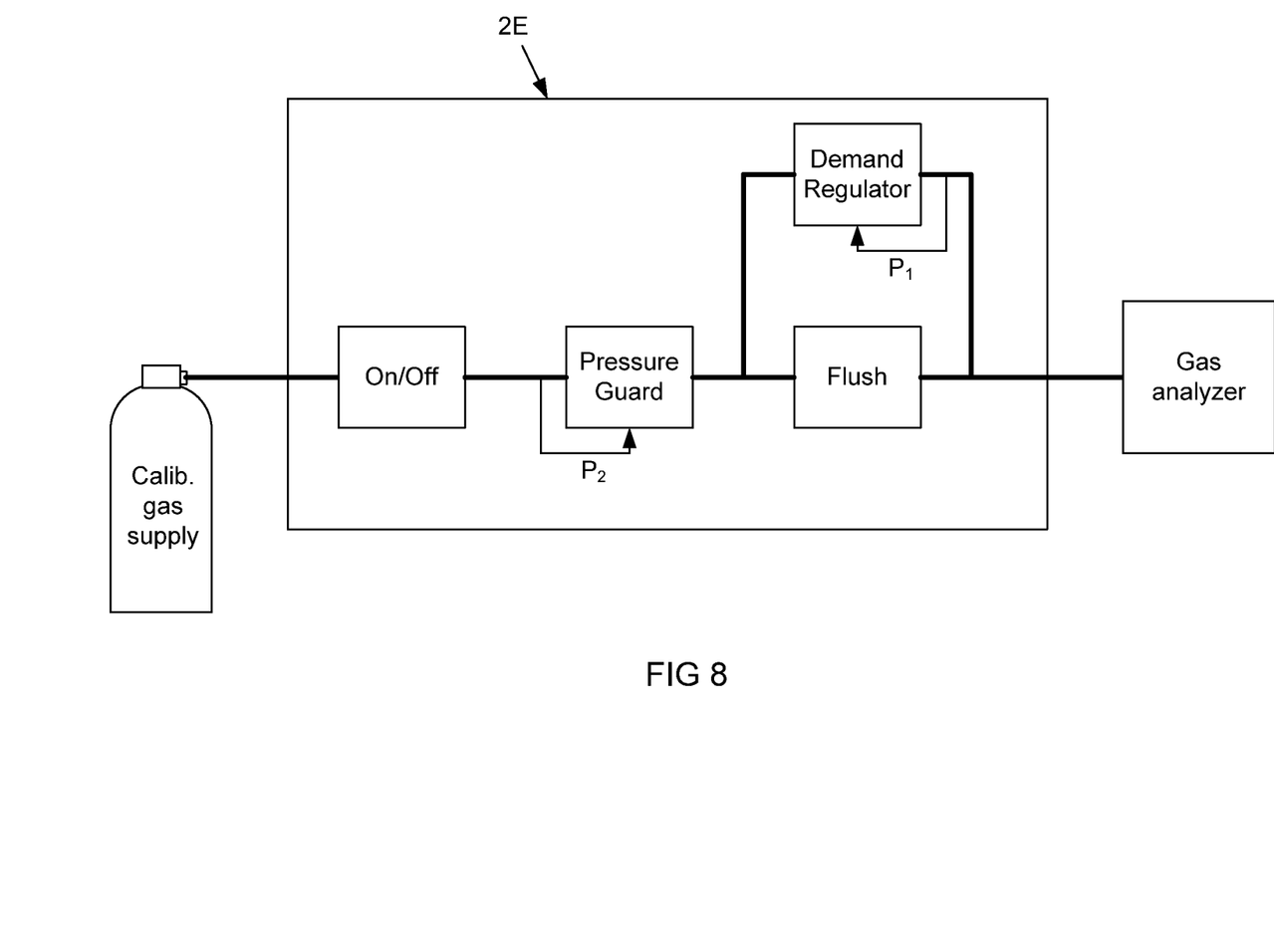
FIG. 8 is a functional view of a gas regulating device according to an embodiment of the invention.

FIG. 8 illustrates a functional view of a gas regulating device 2E according to an embodiment of the invention. The gas regulator 2E is connected between a calibration gas supply and a gas analyzer. The gas regulating device 2E embodies an gas-on-demand functionality denoted 'Demand Regulator', which functionality allows calibration gas to be delivered to the gas analyzer only when a gas pressure $P_1$, downstream of the Demand Regulator, falls below a certain threshold value which herein is referred to as the negative pressure threshold value. The gas regulating device 2E may further embody a flush functionality denoted 'Flush', which functionality allows the gas-on-demand functionality to be "overruled" such that calibration gas can be delivered to the gas analyzer no matter the pressure $P_1$. Furthermore, the gas regulating device 2E may have a pressure-guard functionality denoted 'Pressure Guard', which functionality allows the calibration gas supply to discharge calibration gas only when a gas pressure $P_2$, upstream of the Pressure Guard, exceeds a certain threshold value which herein is referred to as the positive pressure threshold value. Finally, the gas regulating device 2E may have an on-off functionality denoted 'On/Off', which functionality serves to set the gas regulating device 2E in either an 'ON' mode in which the other functionalities of the gas regulating device 2E are unaffected, or an 'OFF' mode in which no calibration gas can ever pass through the gas regulating device 2E.

Although modifications and changes may be suggested by those skilled in the art, it is the intention of the inventors to embody within the patent warranted heron all changes and modifications as reasonably and properly come within the scope of their contribution to the art.

We claim as our invention:

1. A gas regulating device comprising:
   an inlet configured to receive a flow of calibration gas from a calibration gas supply;
   an outlet configured to pass on said flow of calibration gas to a gas analyzer to be calibrated by said calibration gas;
   a gas flow path between said inlet and said outlet, and at least one valve in said gas flow path through which said flow of calibration gas passes between said inlet and said outlet; and
   a valve regulator configured to regulate said at least one valve to permit gas to flow between said inlet and said outlet only when a gas pressure in said gas flow path between said at least one valve and said outlet falls below a first predetermined threshold value, and when a gas pressure in said gas flow path between said inlet and said at least one valve exceeds a second predetermined threshold value.

2. A gas regulating device as claimed in claim 1 comprising a manually actuatable flush actuator configured, when actuated manually, to set said valve regulator to a mode in which said valve regulator regulates said at least one valve to permit gas to flow in said gas flow path between said inlet and said outlet independently of said gas pressure between said at least one valve and said outlet.

3. A gas regulating device as claimed in claim 1 comprising a manually actuatable on-off switching actuator configured, when manually actuated, to set said valve regulator to a mode in which said valve regulator permits no gas to flow in said gas flow path between said inlet and said outlet.

4. A gas regulating device as claimed in claim 1 comprising a housing in which said gas flow path, said at least one valve and said valve regulator are located as a self-contained unit, and wherein said inlet comprises an inlet connection configured to detachably connect said inlet to said calibration gas supply, and wherein said outlet comprises an outlet connection configured to detachably connect said outlet to said gas analyzer.

5. A gas regulating device as claimed in claim 4 wherein said inlet connection is configured to directly connect said inlet with said calibration gas supply with no intervening conduit.

6. A gas regulating device as claimed in claim 1 comprising a calibration gas manometer configured to provide visual indication of said pressure in said gas flow path between said inlet and said at least one valve.

7. A calibration arrangement comprising:
   a calibration gas supply;
   a gas analyzer; and
   a gas regulating device comprising an inlet configured to receive a flow of calibration gas from said calibration gas supply, an outlet configured to pass on said flow of calibration gas to said gas analyzer to be calibrated by said calibration gas, a gas flow path between said inlet and said outlet, and at least one valve in said gas flow path through which said flow of calibration gas passes between said inlet and said outlet, and a valve regulator configured to regulate said at least one valve to permit gas to flow between said inlet and said outlet only when a gas pressure in said gas flow path between said at least one valve and said outlet falls below a first predetermined threshold value, and when a gas pressure in said gas flow path between said inlet and said at least one valve exceeds a second predetermined threshold value.

8. A calibration arrangement as claimed in claim 7 comprising a housing in which said gas flow path, said at least one valve and said valve regulator are located as a self-contained unit, and wherein said inlet comprises an inlet connection configured to detachably connect said inlet to said calibration gas supply, and wherein said outlet comprises an outlet connection configured to detachably connect said outlet to said gas analyzer.

9. A calibration arrangement as claimed in claim 8 wherein said inlet connection is configured to directly connect said inlet with said calibration gas supply with no intervening conduit.

10. A calibration arrangement as claimed in claim 8 wherein said gas flow path has no outlet for said calibration gas.

11. A method for calibrating a gas analyzer, comprising:
providing a gas flow path between an inlet configured to receive a flow of calibration gas from a calibration gas supply and an outlet configured to pass on said flow of calibration gas to a gas analyzer to be calibrated by said calibration gas;
in said gas flow path, providing at least one valve in said gas flow path through which said flow of calibration gas passes between said inlet and said outlet; and
regulating said at least one valve to permit gas to flow between said inlet and said outlet only when a gas pressure in said gas flow path between said at least one valve and said outlet falls below a first predetermined threshold value, and when a gas pressure in said gas flow path between said inlet and said feast one valve exceeds a second predetermined threshold value.

* * * * *